(12) United States Patent
Jung et al.

(10) Patent No.: US 7,679,743 B1
(45) Date of Patent: Mar. 16, 2010

(54) APPARATUS FOR MEASURING MAGNITUDE OF DEFLECTED PROBE BEAM SIGNAL GENERATED BY LASER-INDUCED BREAKDOWN AND METHOD OF MEASURING SIZE OF NANOPARTICLES USING FREQUENCY DISTRIBUTION CURVE OF MAGNITUDE OF PROBE BEAM DEFLECTION SIGNAL

(75) Inventors: Euo Chang Jung, Daejeon (KR); Hye-Ryun Cho, Daejeon (KR); Kyoung Kyun Park, Daejeon (KR); Jei-Won Yeon, Daejeon (KR); Kyuseok Song, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 12/345,424

(22) Filed: Dec. 29, 2008

(30) Foreign Application Priority Data

Jan. 31, 2008 (KR) ........................ 10-2008-0009957

(51) Int. Cl.
    *G01N 15/02* (2006.01)
(52) U.S. Cl. .................. 356/335; 356/336; 356/337; 356/441
(58) Field of Classification Search ......... 356/335–343, 356/432–440, 39–43, 401; 250/573, 574, 250/578.1, 458.1; 382/148, 190, 273
    See application file for complete search history.

(56) References Cited

U.S. PATENT DOCUMENTS

| | | | | | |
|---|---|---|---|---|---|
| 5,316,983 | A | | 5/1994 | Fujimori et al. | |
| 5,813,987 | A | * | 9/1998 | Modell et al. | 600/473 |
| 5,844,685 | A | * | 12/1998 | Gontin | 356/433 |
| 5,861,951 | A | * | 1/1999 | Uesugi et al. | 356/338 |
| 5,936,739 | A | * | 8/1999 | Cameron et al. | 356/441 |
| 5,943,130 | A | * | 8/1999 | Bonin et al. | 356/336 |
| 6,321,111 | B1 | * | 11/2001 | Perelman et al. | 600/477 |
| 6,795,179 | B2 | * | 9/2004 | Kumar | 356/318 |
| 6,906,799 | B2 | * | 6/2005 | Bonin et al. | 356/336 |
| 7,006,682 | B1 | * | 2/2006 | Moriya et al. | 382/145 |
| 7,230,703 | B2 | * | 6/2007 | Sezginer et al. | 356/401 |
| 7,463,364 | B2 | * | 12/2008 | Yacoubian | 356/502 |

FOREIGN PATENT DOCUMENTS

KR    100820776    4/2008

OTHER PUBLICATIONS

Hye-Ryun, Cho et al.,"Probe Between Detection of Laser-Induced Breakdown for Measuring Solubility of Actinide Compounds," *Japanese Journal of Applied Physics*, vol. 47(5):3530-3532 (2008).

* cited by examiner

*Primary Examiner*—Sang Nguyen
(74) *Attorney, Agent, or Firm*—Lahive & Cockfield, LLP; EuiHoon Lee, Esq.

(57) ABSTRACT

The present invention relates to an apparatus and method for measuring the size of nanoparticles present in an aqueous solution as an infinitesimal quantity, and, more particularly, to a scheme that remotely measures the laser-induced breakdown of a fine nanoparticle using a probe beam in a non-contact manner, performs curve fitting on the symmetrical frequency distribution curve of the measured magnitude of a probe beam signal to form the shape of a Gaussian function, obtains calibration curves for the size of the nanoparticle from the peak and full-width at half-maximum thereof, and determines the size of an unknown nanoparticle from the calibration curves.

14 Claims, 10 Drawing Sheets

APPARATUS FOR MEASURING MAGNITUDE OF DEFLECTED PROBE BEAM SIGNAL GENERATED BY LASER-INDUCED BREAKDOWN AND METHOD OF MEASURING SIZE OF NANOPARTICLES USING FREQUENCY DISTRIBUTION CURVE OF MAGNITUDE OF PROBE BEAM DEFLECTION SIGNAL

CROSS-REFERENCE TO RELATED PATENT APPLICATION

This application claims the benefit of Korean Patent Application No. 10-2008-0099572, filed on Oct. 10, 2008, in the Korean Intellectual Property Office, the disclosure of which is incorporated herein in its entirety by reference.

BACKGROUND OF THE INVENTION

1. Field of the Invention

The present invention relates, in general, to an apparatus and method for measuring the size of fine nanoparticles present in an aqueous solution as an infinitesimal quantity, and, more particularly, to a scheme that remotely measures the laser-induced breakdown of fine nanoparticles using a probe beam in a non-contact manner, and measures the size of nanoparticles using the frequency distribution curve of the magnitude of a probe beam signal deflected by the laser-induced breakdown. This scheme is a technology that uses a principle by which the path of a probe beam is changed by a laser-induced shock wave accompanying the occurrence of the laser-induced breakdown, and that enables the sizes of nanoparticles to be discriminated by measuring the magnitudes of probe beam signals.

Further, the present invention proposes a method that sets experimental conditions such that the frequency distribution curve of the magnitude of a deflected probe beam signal is a horizontally symmetrical shape, and performs curve fitting on data about the measured magnitude of the deflected probe beam signal to form a normal distribution curve having the shape of a Gaussian function, thus more easily quantifying the peak and full-width at half-maximum of a frequency distribution curve proportional to the diameter of nanoparticles.

2. Description of the Related Art

A technology that has been generally used to measure colloidal nanoparticles present in an aqueous solution is a method of allowing a Continuous Wave (CW) laser beam to be incident on a sample and measuring the intensity of light scattered from the particles. Most turbidimeters and particle size analyzers that are currently commercialized and sold adopt such a light scattering intensity measurement method. When a particle having a size of larger than 100 nm is intended to be measured, it is possible to use a commercial device that adopts the measurement of light scattering intensity. However, when a fine nanoparticle having a size of smaller than 100 nm is intended to be measured using the above commercial device, there is a limitation in that reliable results can be obtained only when the particle density is above several Parts Per Million (ppm). The reason for this is that, as the particle size decreases, light scattering intensity greatly decreases, so that measurement is possible only under the condition that a relatively larger number of particles instead of a large-size particle can contribute to scattering. Therefore, when fine nanoparticles having a density of less than several ppm are intended to be measured, a device having better sensitivity than the commercial device which adopts the measurement of light scattering intensity must be employed.

Accordingly, in order to measure a nanoparticle with high sensitivity, Laser-Induced Breakdown Detection (LIBD) technologies, for example, U.S. Pat. No. 5,316,983 (1994), German Patent No. DE19833339C1 (2000), and Korean Patent No. 10-0820776 (2008) filed by the present applicant, have been proposed. Such an LIBD technology is a technology using the principle by which laser-induced plasma is generated in the focal region of a lens when a pulse laser beam having a temporal width of several nanoseconds is incident on a sample using the lens. Since the energy of a laser beam required to generate laser-induced plasma increases in the order of solid, liquid and gas, only colloidal nanoparticles contained in the aqueous solution are broken down by using the energy of a suitable laser beam, and thus can be generated in the state of laser-induced plasma. When LIBD technology is used, the limits of the detection of the size and density of nanoparticles are about several nm and several Parts Per Trillion (ppt), respectively, and very excellent measurement sensitivity can be realized compared to a commercial device that adopts the measurement of light scattering intensity.

In LIBD technology, in order to detect laser-induced plasma, a laser-induced shock wave or a plasma flash inevitably accompanying the generation of the laser-induced plasma must be measured. For this measurement, a method of firmly attaching a piezoelectric transducer (PZT) to a sample cell and acoustically measuring a laser-induced shock wave, a method of installing a Charge Coupled Device (CCD) camera near a sample cell and optically measuring a flash appearing when laser-induced plasma is generated, and a method of passing a probe beam through a sample cell and optically measuring a laser-induced shock wave, have been independently developed.

In LIBD technology, the size of a particle can be determined under two different experimental conditions.

First, under an experimental condition that the pulse energy of a laser beam changes, the size of a nanoparticle can be determined by measuring threshold energy defined as minimum laser beam pulse energy required to generate laser-induced plasma. This method uses a principle by which, as the size of a particle increases, threshold energy decreases. Generally, threshold energy can be measured by representing breakdown probability by a function of the pulse energy of a laser beam. Breakdown probability is defined as a value obtained by dividing the number of times that laser-induced breakdown occurs by the total number of incident laser beam pulses. For particles having the same size, as the particle density increases, the breakdown probability thereof increases.

Second, under an experimental condition that the pulse energy of a laser beam is fixed, a method using the frequency distribution curve of the magnitude of a PZT signal and a method using the spatial distribution of a plasma flash measured using a CCD camera have been developed.

However, the method of determining the size of a nanoparticle using the frequency distribution curve of the magnitude of a PZT signal is disadvantageous in that it is difficult to obtain reproducible data due to characteristics that a PZT is directly attached to a sample cell to measure a shock wave. That is, the reason for this disadvantage is that, when samples having particles of different sizes are contained in different sample cells, there is a difficulty when the magnitudes of signals are compared with each other by firmly attaching PZTs to a plurality of different sample cells under the same condition.

The method using the spatial distribution of a plasma flash is advantageous in that reproducible data can be obtained compared to the method using the frequency distribution of the magnitude of a PZT signal. However, this method is inconvenient because several application cases are required in that a high-magnification lens array system must be installed near a sample cell in order to record a flash in a camera pixel having a limited size. For example, when elements harmful to human bodies, such as radioactive substances, and ultra-clean water are used as samples, the samples must be located in a special environment isolated from the surroundings (in a glove box or in a cleaning booth), so that it is undesirable to install a high-magnification lens array system occupying a large space near the sample cells.

Therefore, the present applicant proposed in Korean Patent No. 10-0820776 a method of determining the size of a nanoparticle by measuring and analyzing the frequency distribution curve of the magnitude of the probe beam signal using a probe beam which can be remotely measured in a non-contact manner, unlike a method using a PZT or a CCD camera. The method using a probe beam signal is intended to use a principle by which the path of a probe beam is changed by a laser-induced shock wave accompanying the occurrence of laser-induced breakdown. Thanks to the characteristics that the peak of a frequency distribution curve is proportional to the diameter of a nanoparticle, the size of the nanoparticle can be determined. Remotely measuring the size of a nanoparticle contained in an aqueous solution using a probe beam in a non-contact manner is advantageous in that the applicability thereof is much better than that of the conventional method using the frequency distribution of the magnitude of a PZT signal or the spatial distribution of a plasma flash.

SUMMARY OF THE INVENTION

Accordingly, the present invention has been made keeping in mind the above problems occurring in the prior art, and an object of the present invention is to provide an apparatus for remotely measuring the laser-induced breakdown of fine nanoparticles using a probe beam in a non-contact manner, and a method of setting experimental conditions such that the frequency distribution curve of the magnitude of a deflected probe beam signal is a horizontally symmetrical shape, and performing curve fitting on the frequency distribution data of the magnitude of the deflected probe beam signal, measured in this way, to form a normal distribution curve having the shape of a Gaussian function, thus more easily quantifying the peak and full-width at half-maximum of a frequency distribution curve proportional to the diameter of nanoparticles.

In order to accomplish the above object, the present invention provides an apparatus for measuring a deflected probe beam signal generated by laser-induced breakdown, comprising a pulse laser for causing a pulse laser beam to be incident into a sample cell, which contains a nanoparticle, along a Z-axis direction; a laser-induced breakdown lens arranged on a path along which the pulse laser beam travels in the Z-axis direction, and configured to cause the pulse laser beam to be focused on an internal location of the sample cell; a probe beam laser for causing a probe beam to be incident on the sample cell in a Y-axis direction perpendicular to a travel path of the pulse laser beam so that the probe beam passes through a location perpendicularly spaced apart in an X-axis direction from a focus of the pulse laser beam by a predetermined distance; a notch filter for blocking a light scattering signal corresponding to a wavelength of the pulse laser beam included in signals of the probe beam having passed through the sample cell; a photodiode for detecting a probe beam signal having passed through the notch filter; a gate integrator for receiving the probe beam signal detected by the photodiode; and a computer for storing data output from the gate integrator.

Preferably, the laser-induced breakdown lens may be installed on an optical bench, which is capable of performing a translational motion along the Z-axis direction.

Preferably, the apparatus may further comprise a probe beam lens installed on an optical path formed in the Y-axis direction before the probe beam travels into the sample cell.

Preferably, the apparatus may further comprise a first iris diaphragm installed upstream of the pulse laser to adjust a diameter of the pulse laser beam; a first linear polarizing plate, a second linear polarizing plate and a beam splitter, sequentially installed downstream of the first iris diaphragm, wherein the first linear polarizing plate is installed to be rotatable and the second linear polarizing plate is installed to fix a direction thereof so as to allow only a polarized laser beam traveling in the X-axis direction to pass therethrough; and an energy meter installed to measure energy of a pulse laser beam reflected from the beam splitter.

Preferably, the apparatus may further comprise a second iris diaphragm installed between the notch filter and the photodiode so that a portion of the probe beam lower than a center portion thereof passes through the second iris diaphragm on an X-Z plane, wherein a center of the second iris diaphragm and a center of the photodiode are collinear.

Further, the present invention provides a method of measuring a size of nanoparticles using a frequency distribution curve of a magnitude of a deflected probe beam signal generated by laser-induced breakdown, comprising a) generating laser-induced plasma by causing a pulse laser beam to be incident on a sample cell, which contains a standard nanoparticle having a known size, in a Z-axis direction so that the pulse laser beam is focused on an internal location of the sample cell, and causing a probe beam to be incident on the sample cell in a Y-axis direction perpendicular to a travel path of the pulse laser beam so that the probe beam passes through an internal location of the sample cell, spaced apart in an X-axis direction from a focus of the pulse laser beam by a predetermined distance; b) measuring signals of the probe beam, deflected by a laser-induced shock wave generated by the laser-induced plasma, using a photodiode; c) adjusting the focus of the pulse laser beam so that two signals, having collided against two walls of the sample cell located on an X-Y plane of the sample cell and then having reached the probe beam, among the deflected probe beam signals measured at b), overlap each other; d) obtaining symmetrical frequency distributions of magnitudes of a first deflected probe beam signal, appearing when the laser-induced shock wave directly reaches the probe beam, and a second deflected probe beam signal obtained at c), among the deflected probe beam signals measured at b), using a gate integrator; e) performing curve fitting on the symmetrical frequency distribution of the magnitude of the first deflected probe beam signal obtained at d) to form a shape of a Gaussian function, and obtaining a peak and a full-width at half-maximum value from the curve-fitted distribution curve; f) repeating a) to e) with respect to a standard nanoparticle having a size differing from that of the standard nanoparticle used at a) to e); g) obtaining calibration curves by causing peaks and full-width at half-maximum values of curve-fitted distribution curves, respectively obtained at e) and f), to correspond to the sizes of the standard nanoparticles, respectively; and h) performing a) to e) with respect to an unknown particle, a size of which is unknown, and determining a size of the unknown nanoparticle using the calibration curves obtained at g).

In addition, the present invention provides a method of measuring a size of nanoparticles using a frequency distribution curve of a magnitude of a deflected probe beam signal generated by laser-induced breakdown, comprising a) generating laser-induced plasma by causing a pulse laser beam to be incident on a sample cell, which contains a standard nanoparticle having a known size, in a Z-axis direction so that the pulse laser beam is focused on an internal location of the sample cell, and causing a probe beam to be incident on the sample cell in a Y-axis direction perpendicular to a travel path of the pulse laser beam so that the probe beam passes through an internal location of the sample cell, spaced apart in an X-axis direction from a focus of the pulse laser beam by a predetermined distance; b) measuring signals of the probe beam, deflected by a laser-induced shock wave generated by the laser-induced plasma, using a photodiode; c) adjusting the focus of the pulse laser beam so that two signals, having collided against two walls of the sample cell located on an X-Y plane of the sample cell and then having reached the probe beam, among the deflected probe beam signals measured at b), overlap each other; d) obtaining symmetrical frequency distributions of magnitudes of a first deflected probe beam signal, appearing when the laser-induced shock wave directly reaches the probe beam, and a second deflected probe beam signal obtained at c), among the deflected probe beam signals measured at b), using a gate integrator; e) performing curve fitting on the symmetrical frequency distribution of the magnitude of the second deflected probe beam signal obtained at d) to form a shape of a Gaussian function, and obtaining a peak and a full-width at half-maximum value from the curve-fitted distribution curve; f) repeating a) to e) with respect to a standard nanoparticle having a size differing from that of the standard nanoparticle used at a) to e); g) obtaining calibration curves by causing peaks and full-width at half-maximum values of curve-fitted distribution curves, respectively obtained at e) and f), to correspond to the sizes of the standard nanoparticles, respectively; and h) performing a) to e) with respect to an unknown particle, a size of which is unknown, and determining a size of the unknown nanoparticle using the calibration curves obtained at g).

Preferably, the method may be performed on a nanoparticle having a size of smaller than 100 nm.

Preferably, among a) to h), at a), a first linear polarizing plate installed to be rotatable and a second linear polarizing plate installed to fix a direction thereof so as to allow only a polarized laser beam traveling in an X-axis direction to pass therethrough may be sequentially arranged on a path of the pulse laser beam before the pulse laser beam is incident on the sample cell, and energy of the pulse laser beam is adjusted by rotating the first linear polarizing plate.

Preferably, at b), a light scattering signal corresponding to a wavelength of the pulse laser beam may be blocked using a notch filter before signals of the probe beam having passed through the sample cell are detected by the photodiode.

Preferably, at b), a lower portion of the probe beam deviating from a center portion thereof may be detected by the photodiode.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Hereinafter, embodiments of the present invention will be described in detail with reference to the attached drawings.

Figure 1:
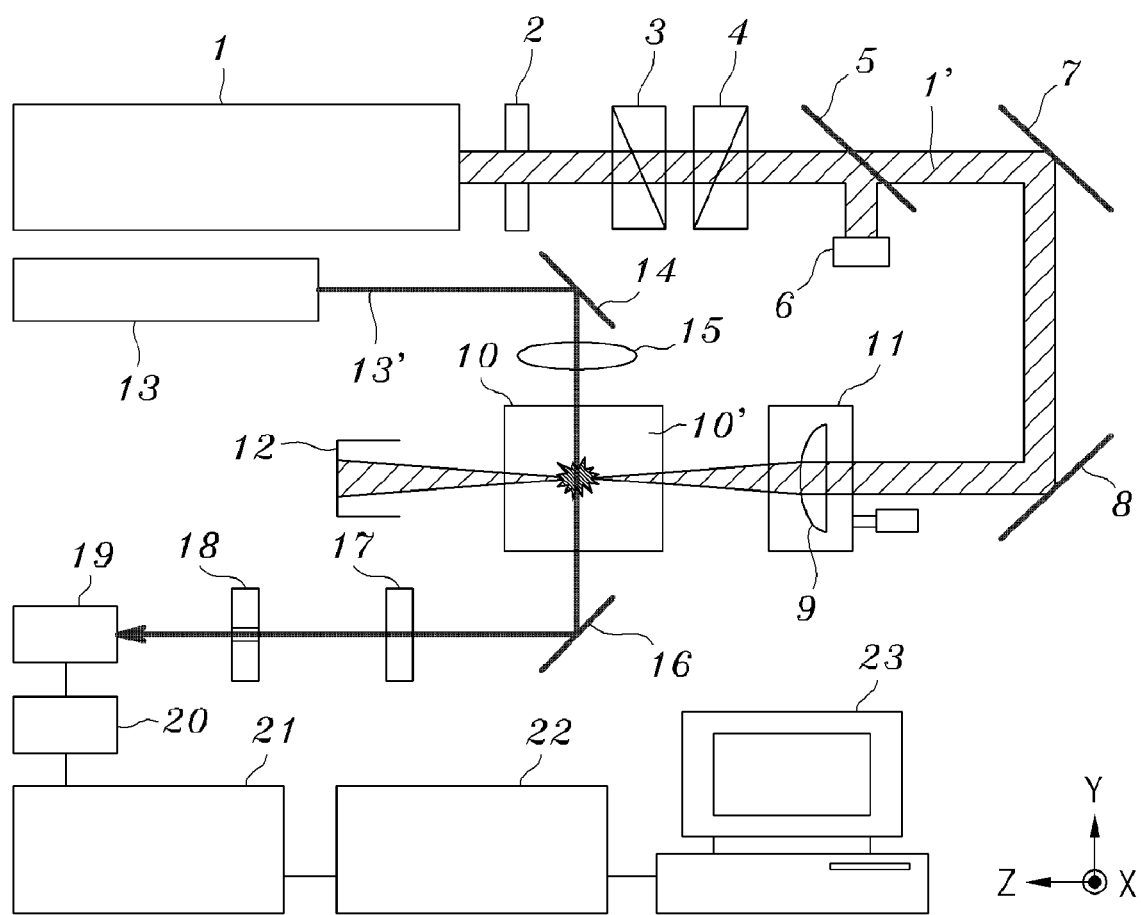
FIG. 1 is a diagram schematically showing the construction of an apparatus for breaking down a nanoparticle in an aqueous solution using a pulse laser beam and an apparatus for measuring a deflected probe beam signal using a probe beam according to the present invention.

In order to accomplish the above object, the present invention is intended to construct the apparatus of FIG. 1, and the functions and operations of respective components are described below.

The second-order harmonic beam (green wavelength of 532 nm) of a Nd:YAG pulse laser 1 having a pulse width of about 6 nanoseconds is used as a light source for laser-induced breakdown. In order to adjust the diameter of a pulse laser beam 1' to 4 mm, a first iris diaphragm 2 is installed on the travel path of the pulse laser beam 1'.

Two linear polarizing plates 3 and 4 required to adjust the energy and polarization of the pulse laser beam 1' are arranged downstream of the first iris diaphragm 2. At this time, the first linear polarizing plate 3 is rotatably installed, and the second linear polarizing plate 4 is installed to fix the direction thereof (X-axis direction in FIG. 1) so that only a polarized laser beam perpendicular to a bottom plane can pass therethrough. Accordingly, the energy of the laser beam 1' incident on the sample 10' can be adjusted by rotating the first polarizing plate. Further, in order to measure the adjusted energy of the laser beam 1', a beam splitter 5 having a reflectivity of about 4% is disposed downstream of the two linear polarizing plates 3 and 4, thus enabling part of the laser beam 1' to be incident on an energy meter 6.

Further, a first mirror 7 and a second mirror 8 are arranged on the path of the laser beam 1' having passed through the beam splitter 5 so that the path of the laser beam 1' can be easily adjusted in a horizontal direction or a vertical direction when the laser beam 1' is incident on the sample 10'. The laser beam 1' having passed through the two mirrors 7 and 8 is focused on an internal location of the sample cell 10 using a laser-induced breakdown lens 9 having a focal length of 40 mm. At this time, in order to adjust the focus of the laser beam 1' formed at the internal location of the sample cell 10, the laser-induced breakdown lens 9 is installed on an optical bench 11 capable of performing a translational motion at a length of 10 mm along a Z axis direction. The laser beam 1' having passed through the sample 10' is blocked by an optical shielding block 12.

Both a flash and a shock wave are simultaneously generated as a result of the generation of laser-induced plasma in a region in which the pulse laser beam 1' is focused. The flash may be measured using a CCD camera and the shock wave may be measured using a Piezoelectric Transducer (PZT) or a probe beam. Compared to the PZT, the probe beam is advantageous in that the shock wave can be remotely measured in a non-contact manner. For this operation, a laser beam generated by a probe beam laser 13 is used as a probe beam 13'. This method is implemented using a principle by which the path of the probe beam 13' is changed due to variation in the refractive index of a medium when a laser-induced shock wave generated near the focus of the pulse laser beam 1' passes through the medium. The change of the path of the probe beam 13' consequently results in a change of the intensity of the probe beam 13' incident on a photodiode 19. In an embodiment of the present invention, a CW He—Ne laser was used as the probe beam laser 13.

The probe beam 13' is incident on the sample cell 10 using both a third mirror 14 and a probe beam lens 15 having a focal length of 150 mm. The probe beam 13' having passed through the sample cell 10 is incident on the photodiode 19 through a fourth mirror 16. In order to prevent a pulse laser beam 1' scattered at the nanoparticles in the sample cell 10 and the sample 10' from being detected by the photodiode 19, a notch filter 17 for blocking the transmission of light having a wavelength of 532 nm is installed. In order to sensitively measure variation in the intensity of the probe beam 13', an iris diaphragm 18 having a diameter of 0.5 mm is installed upstream of the photodiode 19. The signal measured by the photodiode 19 is electrically amplified by an amplifier 20, and the waveform of the signal of the probe beam 13' amplified by the amplifier 20 can be measured using an oscilloscope 21. In order to measure the magnitude of the signal of the probe beam 13', a gate integrator 22 is used. An electrical signal from the gate integrator 22 is stored in a computer 23. The gate integrator 22 is a circuit for obtaining a pulse having a magnitude proportional to the integrated value of a signal pulse within a designated time.

Figure 2:
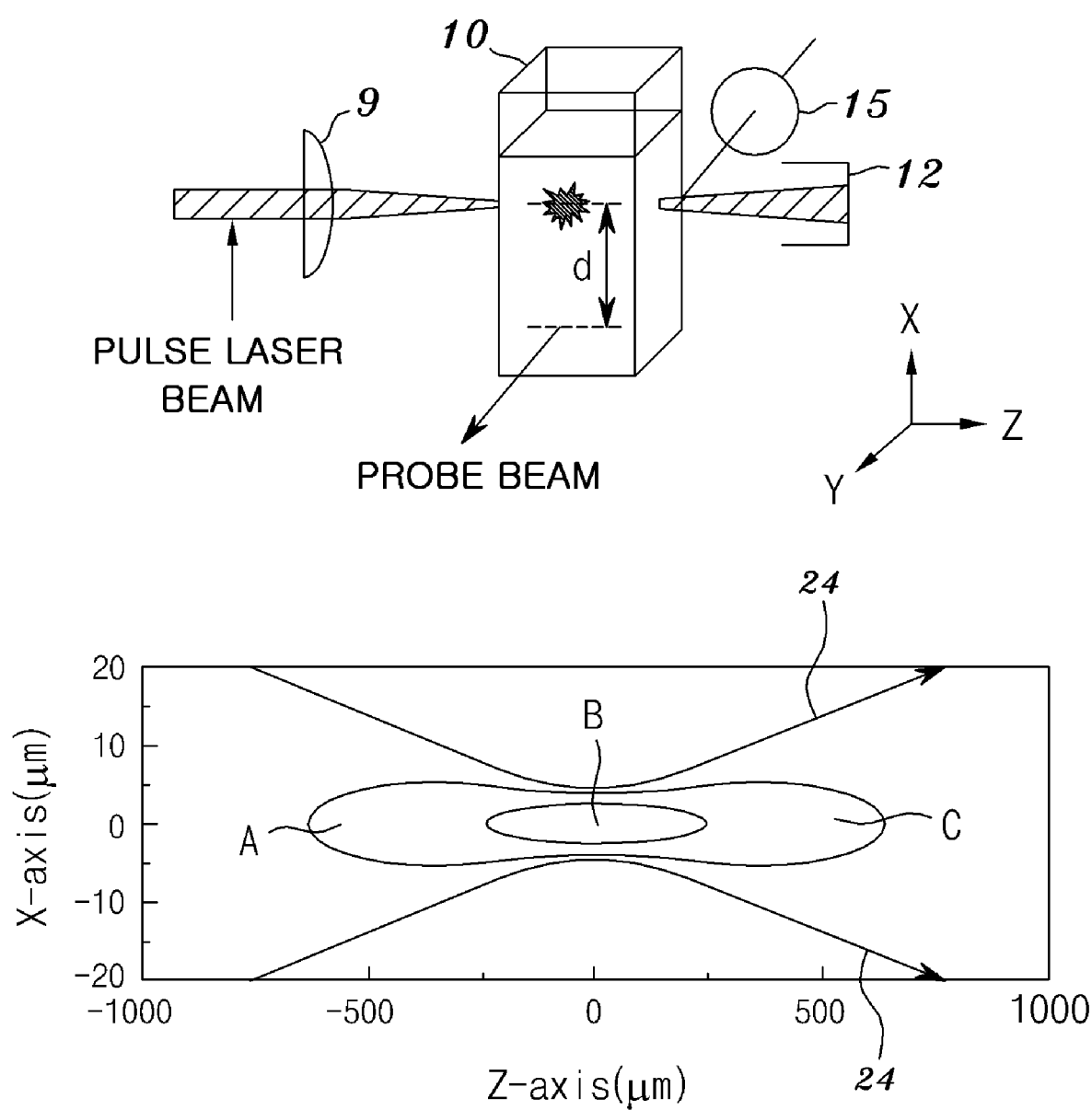
FIG. 2 illustrates a schematic diagram showing the direction of a pulse laser beam (Z-axis direction) used for the breakdown of a nanoparticle, the direction of a probe beam (Y axis direction) traveling in a direction perpendicular to the Z axis direction, and the distance between the two beams, and an enlarged diagram showing the focal region of a pulse laser beam formed by a lens.

Details of the focal region of the pulse laser beam 1' and the path of the probe beam 13' in the sample cell 10 are shown in FIG. 2. Laser-induced breakdown occurs due to the laser-induced breakdown lens 9 having a focal length of 40 mm at the location on which the pulse laser beam 1' traveling in the Z-axis direction is focused. The probe beam 13' passes by a location, which is below the focus of the pulse laser beam 1' by a predetermined distance d in the X-axis direction, in the Y-axis direction (a direction perpendicular to the pulse laser beam). The probe beam 13' is focused on an internal location of the sample cell 10 by the probe beam lens 15 having a focal length of 150 mm. Whether the probe beam lens 15 is used greatly influences the symmetry of the frequency distribution curve of the signal magnitude of the probe beam 13'.

In FIG. 2, a hyperbolic curve 24 indicated by an arrow is a result obtained by calculating the laser beam power density (irradiance) of the focal region with respect to a Z-X plane when the pulse laser beam 1', which has a diameter of 4 mm and the spatial distribution (X-Y plane) of the power of which has the shape of a Gaussian function, passes through the laser-induced breakdown lens 9 and then travels in the Z-axis direction. The origin of coordinates denotes a location on which the pulse laser beam 1' is focused. In respective contour lines having the shapes of an ellipse and a peanut, region "B" indicates a central region having high power density, and regions "A" and "C" indicate regions in which the power density of the pulse laser beam 1' decreases in a direction away from the origin. Therefore, in the case where laser-induced breakdown occurs in region "B", the magnitude of the signal of the probe beam 13' is greater than that of the case where laser-induced breakdown occurs in regions "A" and "C".

Figure 3A:
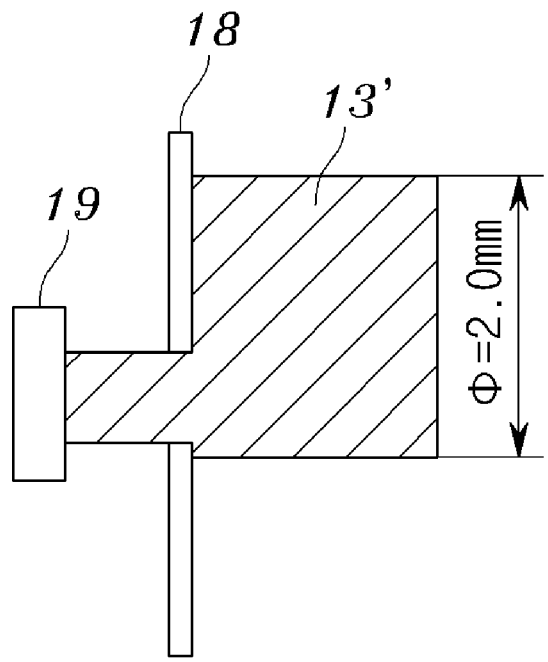
FIGS. 3A and 3B are diagrams schematically showing the locations of an iris diaphragm and a detector used to increase the sensitivity of signals in the deflected probe beam signal measurement apparatus according to the present invention.
Figure 3B:
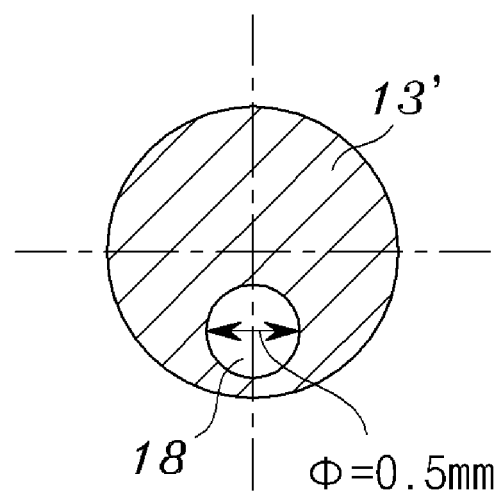

FIGS. 3A and 3B illustrate a procedure for selecting the location of the second iris diaphragm 18 to improve sensitivity when the signal of the probe beam 13' is measured. The probe beam 13' traveling in the Y-axis direction has a diameter of about 2 mm. The second iris diaphragm 18 having a diameter of 0.5 mm is installed upstream of the photodiode 19, but it is installed so that a portion of the probe beam 13' lower than the center portion thereof passes through the second iris diaphragm 18 on the X-Z plane, as shown in FIG. 3B. Further, the center of the second iris diaphragm 18 and the center of the photodiode 19 are collinear, as shown in FIG. 3A. When the center portion of the probe beam 13' and the center of the second iris diaphragm 18 are not coincident with each other, and the lower portion of the probe beam 13' is caused to pass through the second iris diaphragm 18, variation in a deflection signal can be more sensitively detected by the photodiode 19 because energy density in the lower portion of the probe beam 13' is relatively lower than that of the center portion.

A shock wave generated in laser-induced plasma has characteristics that the velocity thereof is changing while the shock wave travels through an aqueous solution medium. At an initial interval during which plasma is generated, the velocity of the shock wave is higher than that of a typical acoustic wave (1486 m/s in the case of an aqueous solution), so that the shock wave exhibits the characteristics of an ultrasonic wave. As the shock wave travels through the medium, its velocity is decreasing, and then the shock wave becomes a typical acoustic wave. Unlike the conventional method of attaching a piezoelectric transducer to a sample cell and measuring a shock wave, the method using the probe beam 13' is capable of separately measuring an ultrasonic wave and an acoustic wave using temporal resolution and spatial resolution depending on the location of the probe beam 13'. This construction can be regarded as another feature of the apparatus constructed according to the present invention.

Figure 4:
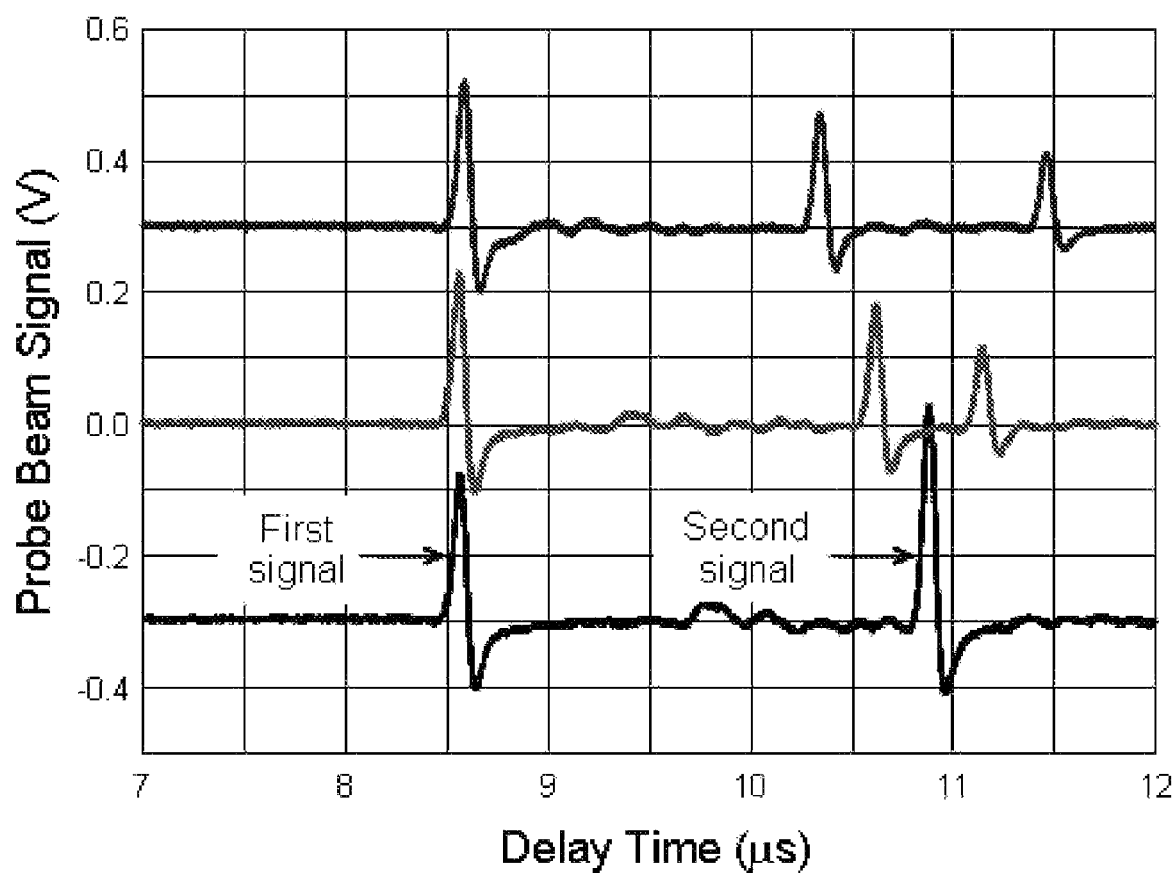
FIG. 4 is a diagram showing the first and second signals of a probe beam signal waveform according to the present invention.

FIG. 4 illustrates signal waveforms measured when the probe beam 13' passes through a location spaced downwardly from the location, at which the laser-induced plasma is generated, by 12.6 mm (portion indicated by 'd' in FIG. 2). In FIG. 4, the origin on an X axis denotes the time at which the pulse laser beam 1' is incident and laser-induced plasma is formed. The waveforms of FIG. 4 show the results obtained by using the probe beam lens 15 under the condition that the probe beam 13' is focused on the same X-Z plane as the plane on which laser-induced breakdown occurs. The three waveforms of FIG. 4 indicate waveforms varying when the location of the laser-induced breakdown lens 9 is finely changed in the Z-axis direction in the state in which the location of the probe beam 13' is fixed. A first probe beam signal appearing at the same time point in common in the three waveforms appears 8.5 μs after the pulse laser beam 1' has been incident in order to cause laser-induced breakdown. Such 8.5 μs corresponds to the time required for an acoustic wave having a velocity of about 1486 m/s to travel a distance of 12.6 mm and thus to reach the location of the probe beam 13'.

In FIG. 4, probe beam signals, appearing after the first probe beam, are formed as the result of an operation in which a shock wave traveling through an aqueous solution medium collides against the wall of the sample cell 10 and then reaches the location of the probe beam 13'. Under the condition that the pulse laser beam 1' travels in the Z-axis direction and the probe beam 13' travels in the Y-axis direction to be perpendicular to each other, it can be seen that the second and third probe beam signals in the uppermost waveform of FIG. 4 appear as the result of an operation in which a shock wave collides against two walls placed on the X-Y plane, among the walls of the sample cell 10, and then reaches the location of the probe beam 13'. Therefore, when the location of the laser-induced breakdown lens 9 is finely changed in the Z-axis direction, the times at which second and third probe beam signals appear change from those depicted by the uppermost waveform to those of the center waveform of FIG. 4. When laser-induced breakdown occurs at the exact midpoint between two walls placed on the X-Y plane, it can be seen from the lowermost waveform of FIG. 4 that two shock waves, having collided against the two walls, reach the location of the probe beam 13' at the same time, and thus the magnitude of the signal increases as a result of the overlapping of signals. Since the distance between the two walls of the sample cell 10 is 10 mm, the travel distance of the shock waves is about 16.1 mm when laser-induced breakdown occurs at the exact midpoint between the two walls of the sample cell 10, and thus the second probe beam signal attributable to overlapping shock waves appears after about 10.8 μs.

Consequently, the locations of the second iris diaphragm 18 and the laser-induced breakdown lens 9 are adjusted, so that the probe beam signal waveform shown in the lowermost waveform of FIG. 4 can be obtained. Even if any one of the two signals appearing in the lowermost waveform is used, the frequency distribution of the magnitude of the probe beam signal can be obtained.

Figure 5:
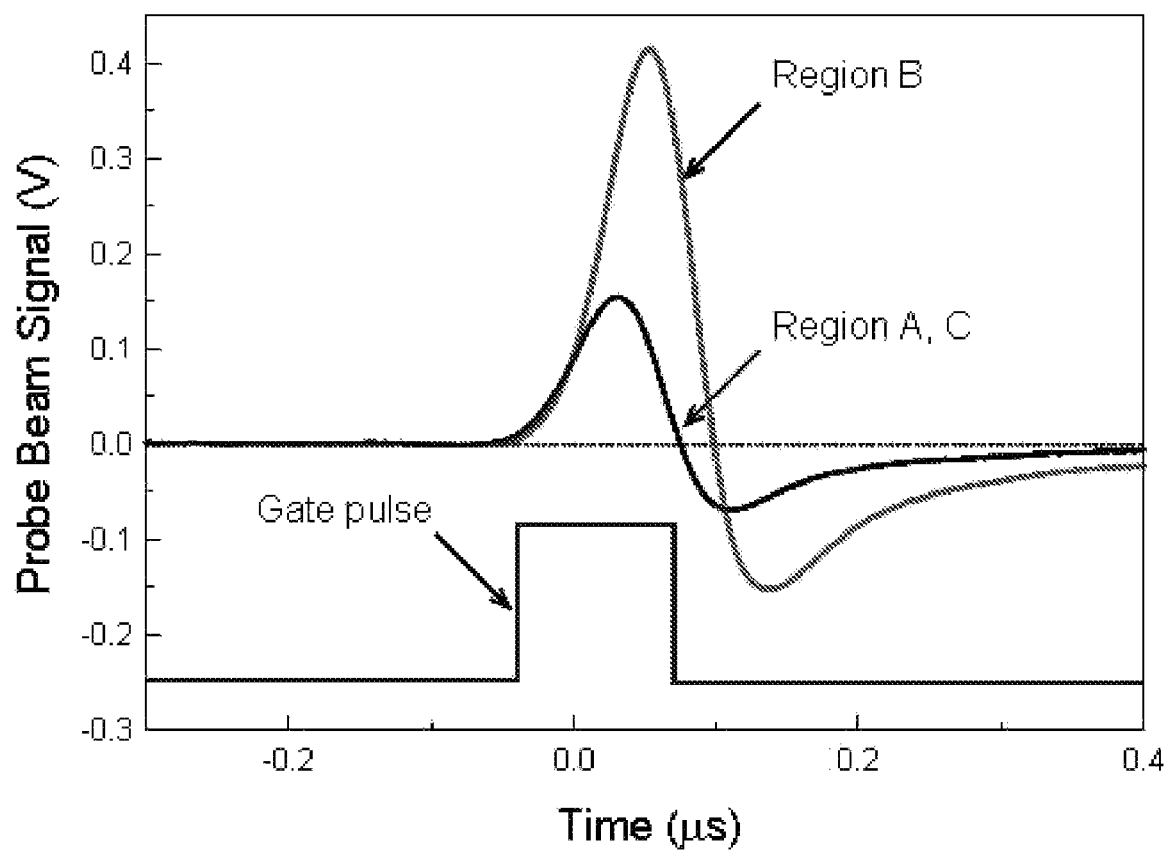
FIG. 5 is a diagram showing the characteristics of the first signal of a probe beam signal waveform, and the location and width of the gate pulse of a gate integrator used to measure the frequency distribution of the magnitude of the probe beam signal.

In FIG. 5, the location and width of the gate integrator 22 selected to measure the magnitude of the first signal of the probe beam waveform and to obtain a frequency distribution curve, are shown. The magnitude of the first signal of the probe beam waveform changes according to the location at which laser-induced plasma is generated. As shown in FIG. 2, when the laser-induced breakdown occurs in the focal region of the pulse laser beam 1' (region "B" in FIG. 2), the magnitude of the probe beam signal is large because the power density of the pulse laser beam 1' is high. Compared to the probe beam signal obtained when laser-induced breakdown occurs in regions (regions "A" and "C" in FIG. 2) surrounding the focal region having relatively low power density, it can be seen that the width of the waveform in the focal region, as well as the magnitude of the signal, are large.

Figure 6:
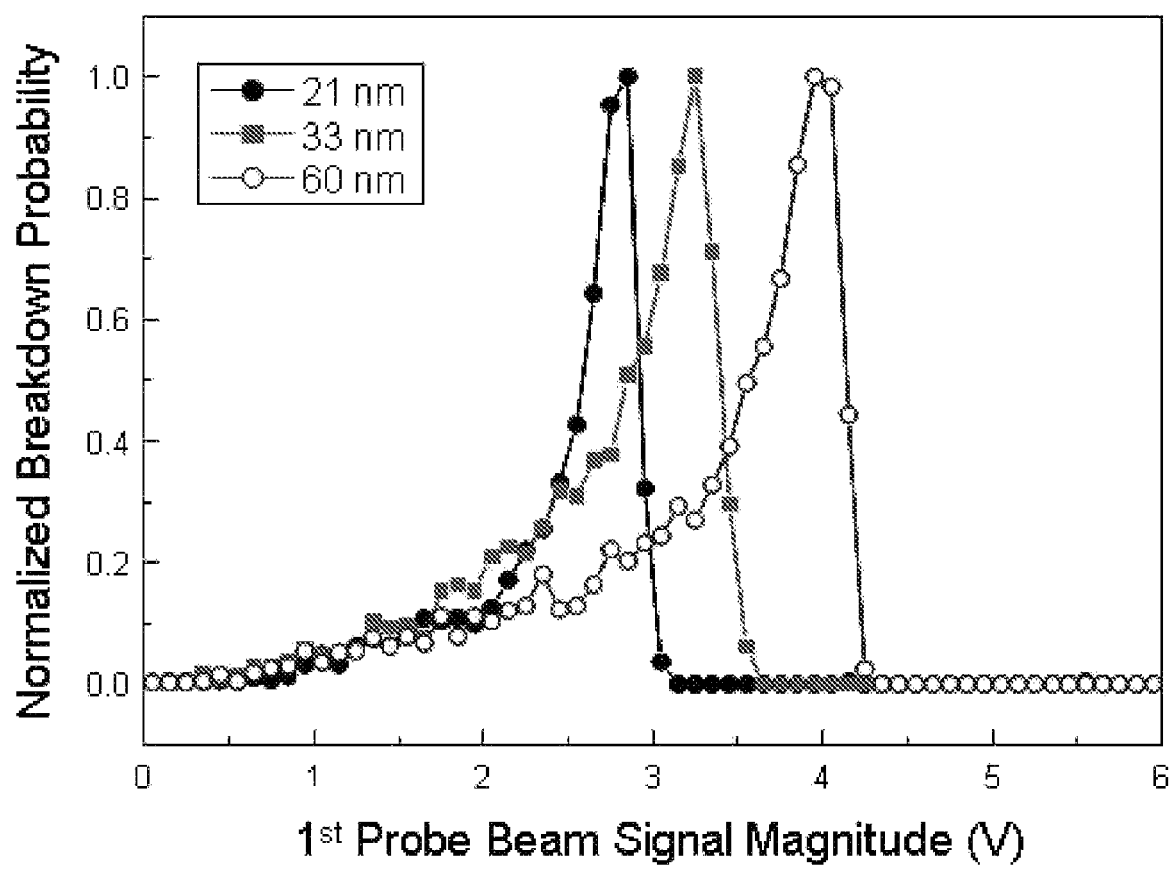
FIG. 6 is a diagram showing an embodiment in which the frequency distribution curve of the magnitude of the first signal of a probe beam signal waveform is measured according to the present invention (when a probe beam lens is used)

FIG. 6 shows the results obtained by measuring the frequency distribution of the magnitude of a probe beam signal with respect to standard nanoparticles having different sizes (polystyrene particles of 21 nm, 33 nm, and 60 nm) under the condition that the location and width of the gate pulse of the gate integrator 22 are fixed, as shown in FIG. 5. In the case of a density condition, the densities of respective particles having sizes of 21, 33, and 60 nm are 1, 2 and 7 Parts Per Billion (PPB), respectively. In FIG. 6, an X axis denotes the magnitude of a probe beam signal, and a Y axis denotes values obtained by equally normalizing the probabilities of laser-induced breakdown of respective standard nanoparticles having different sizes to 1.0. The interval of the X axis during which data is processed to form a frequency distribution curve is 0.1 V. As the size of a standard nanoparticle increases, an aspect in which the peak and full-width at half-maximum of a frequency distribution curve increase can be exhibited. Therefore, when the peaks of different frequency distribution curves are used depending on the sizes of particles, calibration curves required for the determination of a particle size can be obtained.

Figure 7:
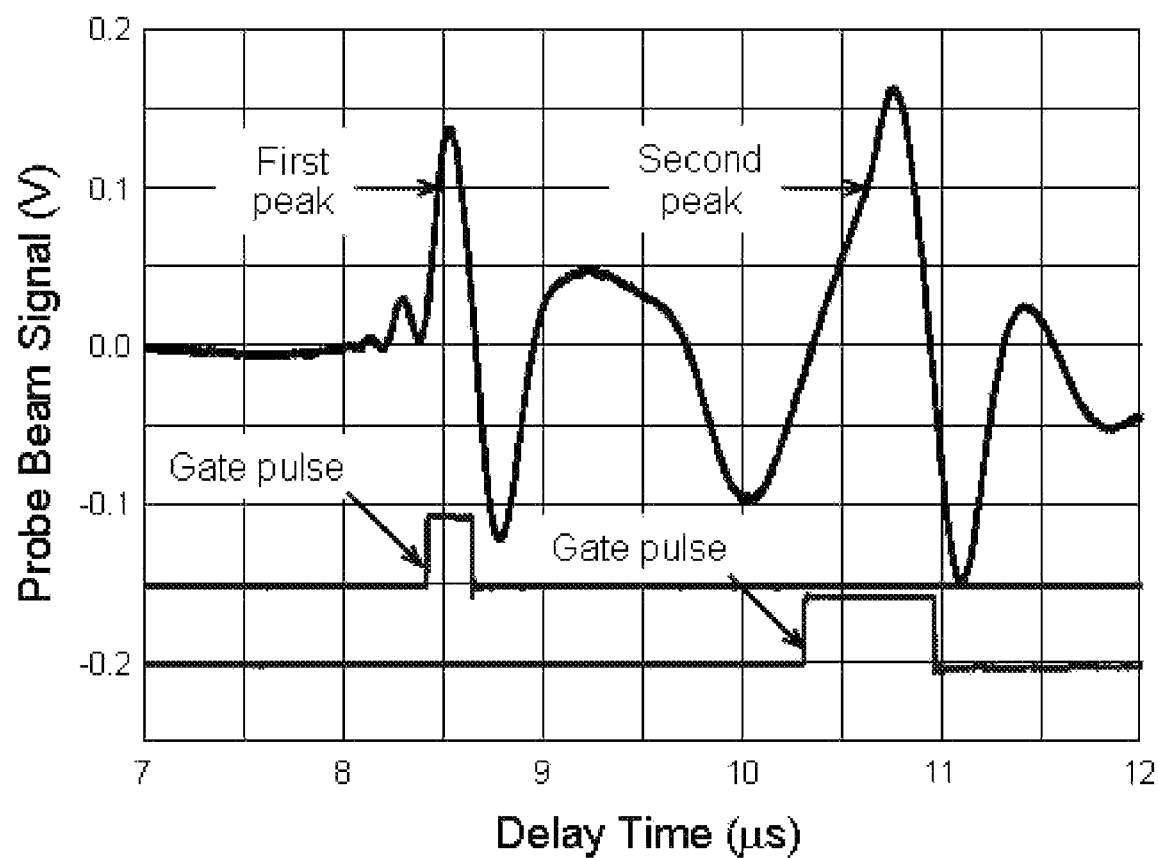
FIG. 7 is a diagram showing the first and second signals of a deflected probe beam signal waveform measured under the condition that a probe beam lens is removed to improve the asymmetrical frequency distribution curve of the magnitude of the first signal of a probe beam signal waveform according to the present invention.

The reason that the frequency distribution curves of FIG. 6 exhibit a horizontally asymmetrical distribution with respect to the peak values thereof on the X axis is that, as described above with reference to FIG. 5, the widths of probe beam signal waveforms differ when laser-induced breakdown occurs in regions (region "B" and regions "A" and "C" of FIG. 2) in which the power densities of the pulse laser beam 1' are different from each other, and thus the magnitudes of probe beam signals measured by the gate integrator 22 are saturated. Therefore, when measurement conditions change so that measurement is less influenced by the width of a probe beam signal waveform and more sensitively reacts to the magnitude of a signal according to the region in which laser-induced breakdown occurs, a frequency distribution curve horizontally symmetrical with respect to the peak on the X axis can be obtained. For this operation, a probe beam signal waveform, measured under the condition that the probe beam lens 15 is removed, is shown in FIG. 7. Compared to the lowermost waveform of FIG. 4, it can be seen that the temporal width of the probe beam signal waveform is widened. Gate pulses set to measure frequency distribution curves of the magnitudes of first and second signals of a probe beam signal waveform are shown together in FIG. 7.

Figure 8:
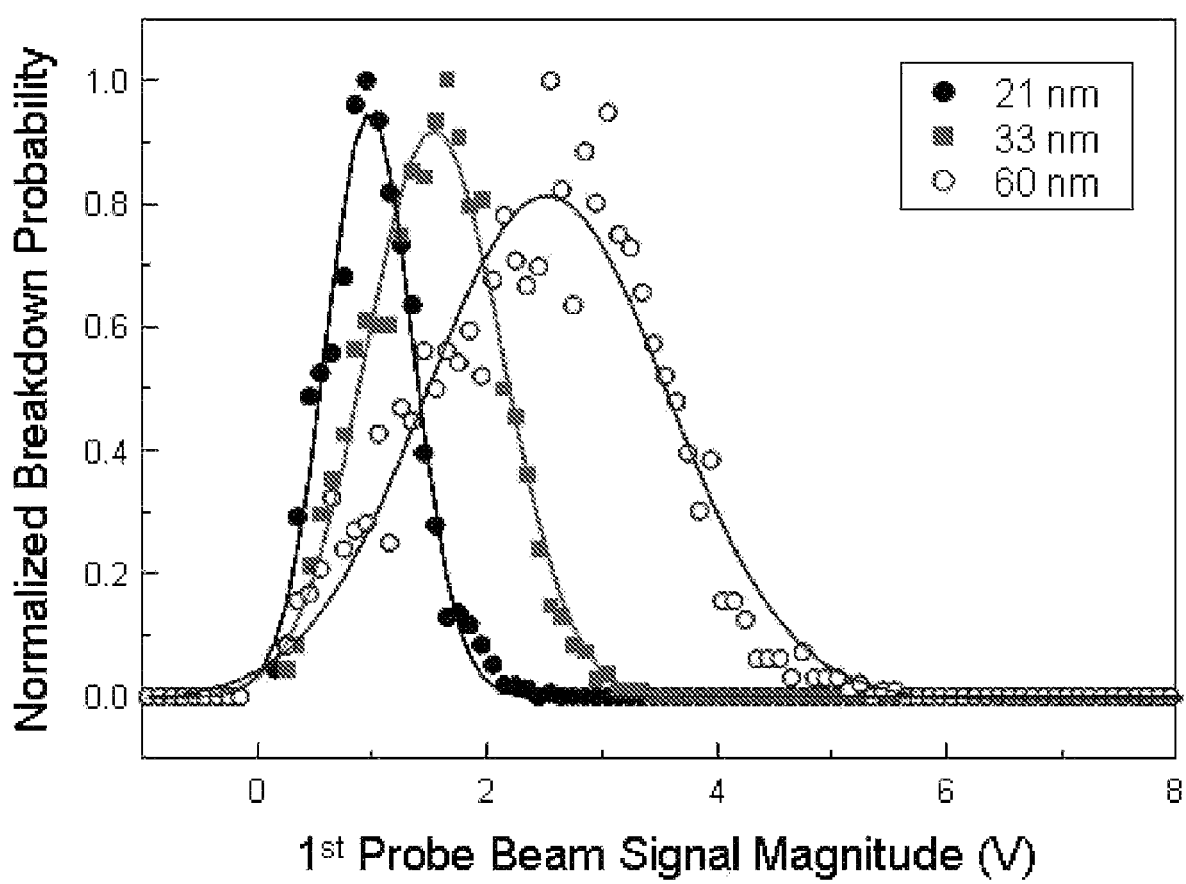
FIG. 8 is a diagram showing an embodiment in which the frequency distribution curve of the magnitude of the first signal of a probe beam signal waveform is measured according to the present invention (when a probe beam lens is not used)

FIG. 8 illustrates the results, obtained by measuring the frequency distributions of the magnitudes of probe beam signals for standard nanoparticles having different sizes (polystyrene particles having sizes of 21 nm, 33 nm, and 60 nm) under the condition that the location and width of the gate pulse of the gate integrator 22 are fixed, as shown in FIG. 7. In FIG. 8, an X axis denotes the magnitude of a probe beam signal, and a Y axis denotes values obtained by normalizing the probabilities of laser-induced breakdown of the three standard nanoparticles having different sizes. Unlike the graph of FIG. 6, frequency distribution curves horizontally symmetrical with respect to the peaks thereof on the X axis can be obtained for all of the particles having different sizes. Since such a frequency distribution curve can be fitted to a normal distribution curve having the shape of a Gaussian function, the graph of FIG. 8 is very useful for the quantification of the peak and full-width at half-maximum of a curve compared to the asymmetrical frequency distribution curve of FIG. 6. Respective solid lines in the drawing are results obtained by performing curve fitting on frequency distribution data, indicated by respective symbols, to the shape of a Gaussian function, and the correlation coefficients therebetween are above 0.95. It can be seen that, as the size of a nanoparticle increases, an aspect in which the peak and full-width at half-maximum of a frequency distribution curve increase is exhibited. Therefore, a calibration curve used to determine the size of a particle can be obtained using the peak and full-width at half-maximum varying according to the size of a particle.

Figure 9:
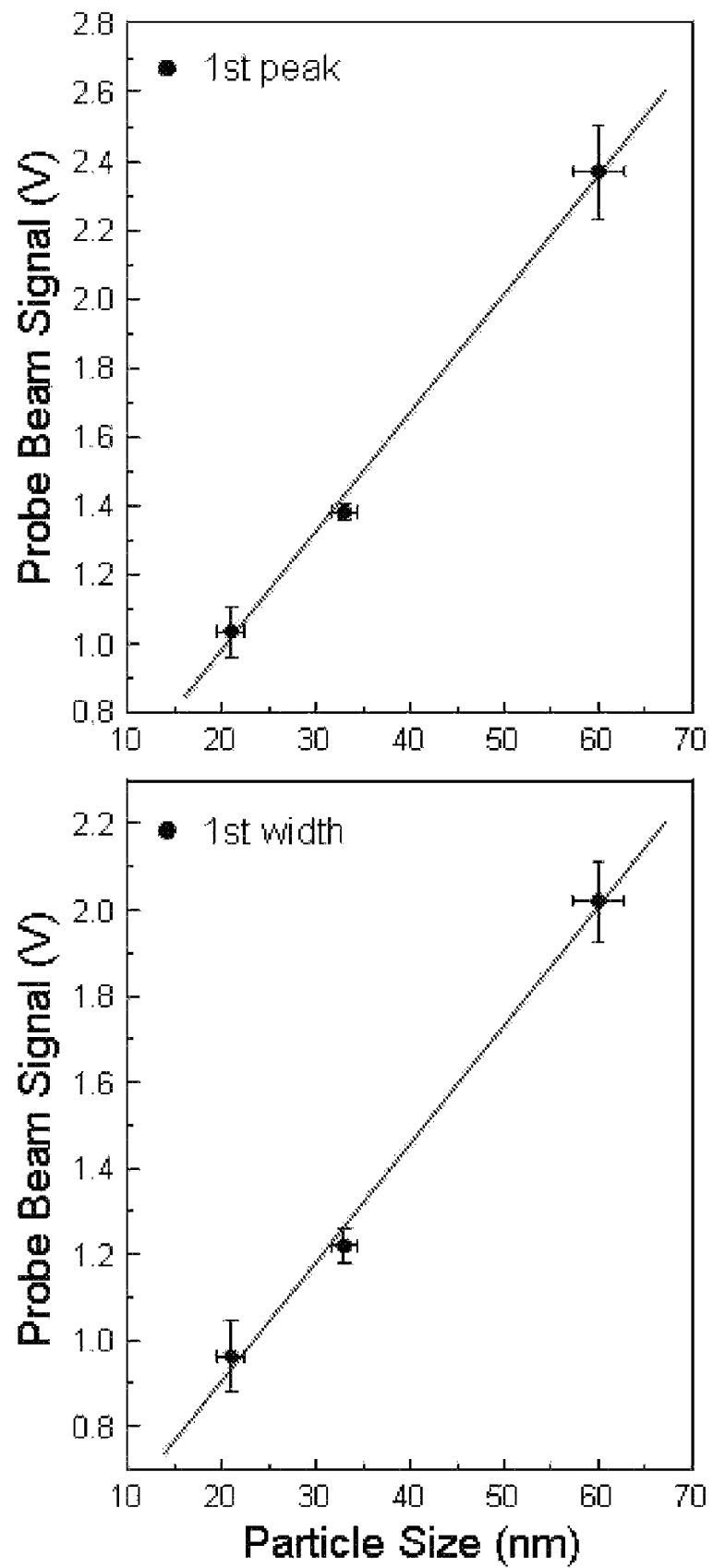
FIG. 9 is a diagram showing an embodiment in which the size of a nanoparticle contained in an aqueous solution is measured using the peak and full-width at half-maximum of the frequency distribution curve of the first signal of a probe beam signal waveform according to the present invention.
Figure 10:
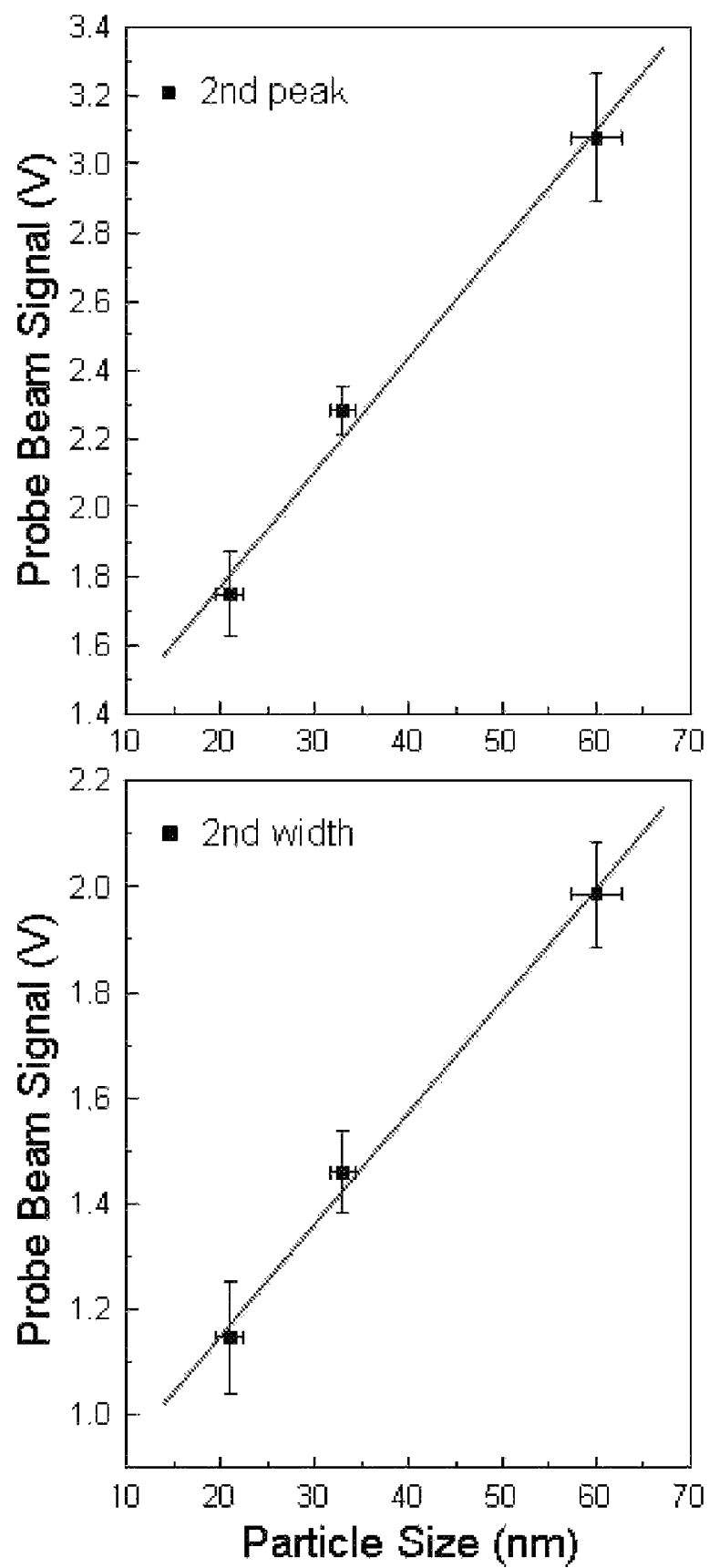
FIG. 10 is a diagram showing an embodiment in which the size of a nanoparticle contained in an aqueous solution is measured using the peak and full-width at half-maximum of the frequency distribution curve of the second signal of a probe beam signal waveform according to the present invention.

Examples in which calibration curves required for the determination of particle sizes are obtained after the frequency distribution curves of first and second signals in the probe beam signal waveform of FIG. 7 have been obtained, as shown in FIG. 8, are shown in FIGS. 9 and 10. Filled symbols in FIGS. 9 and 10 are mean values obtained by repeating experiments on a single particle three or more times, and the standard deviations thereof are represented by error symbols, that is, crutch cross symbols. The solid lines of FIGS. 9 and 10 are results obtained using a least square fitting method to verify the linearity of data, and exhibit very excellent linearity in which the correlation coefficients therebetween are 0.99. Therefore, when the calibration curves of FIGS. 9 and 10 are used, information about the sizes of particles of unknown nanoparticle samples can be known from the peaks and full-width at half-maximum values of the frequency distribution curves of the magnitudes of probe beam signals for the nanoparticle samples. The results of FIGS. 9 and 10 prove that the sizes of nanoparticles can be discriminated by analyzing the distribution of the magnitude of a laser-induced shock wave measured using the probe beam 13'. These examples are merely presented for easy understanding of the present invention, and the method of the present invention is not limited to the case of standard nanoparticles used in the present embodiment.

As described above, the present invention is advantageous in that it remotely measures the laser-induced breakdown of a fine nanoparticle using a probe beam in a non-contact manner, and sets experimental conditions to allow the frequency distribution curve of the measured magnitude of a deflected probe beam signal to be a horizontally symmetrical shape, so that curve fitting can be performed on data of the magnitude of a deflected probe beam signal to form a normal distribution curve having the shape of a Gaussian function, thus more easily quantifying the peak and full-width at half-maximum of a frequency distribution curve proportional to the diameter of a nanoparticle.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for measuring a deflected probe beam signal generated by laser-induced breakdown, comprising:
 a pulse laser for causing a pulse laser beam to be incident into a sample cell, which contains a nanoparticle, along a Z-axis direction;
 a laser-induced breakdown lens arranged on a path along which the pulse laser beam travels in the Z-axis direction, and configured to cause the pulse laser beam to be focused on an internal location of the sample cell;
 a probe beam laser for causing a probe beam to be incident on the sample cell in a Y-axis direction perpendicular to a travel path of the pulse laser beam so that the probe beam passes through a location perpendicularly spaced apart in an X-axis direction from a focus of the pulse laser beam by a predetermined distance;
 a first iris diaphragm installed upstream of the pulse laser to adjust a diameter of the pulse laser beam;
 a first linear polarizing plate, a second linear polarizing plate and a beam splitter, sequentially installed downstream of the first iris diaphragm, wherein the first linear polarizing plate is installed to be rotatable and the second linear polarizing plate is installed to fix a direction thereof so as to allow only a polarized laser beam traveling in the X-axis direction to pass therethrough;
 an energy meter installed to measure energy of a pulse laser beam reflected from the beam splitter;
 a notch filter for blocking a light scattering signal corresponding to a wavelength of the pulse laser beam included in signals of the probe beam having passed through the sample cell;
 a photodiode for detecting a probe beam signal having passed through the notch filter;
 a gate integrator for receiving the probe beam signal detected by the photodiode; and
 a computer for storing data output from the gate integrator.

2. The apparatus according to claim 1, wherein the laser-induced breakdown lens is installed on an optical bench, which is capable of performing a translational motion along the Z-axis direction.

3. The apparatus according to claim 1, further comprising a probe beam lens installed on an optical path formed in the Y-axis direction before the probe beam travels into the sample cell.

4. The apparatus according to claim 1, further comprising a second iris diaphragm installed between the notch filter and the photodiode so that a portion of the probe beam lower than a center portion thereof passes through the second iris diaphragm on an X-Z plane, wherein a center of the second iris diaphragm and a center of the photodiode are collinear.

5. A method of measuring a size of nanoparticles using a frequency distribution curve of a magnitude of a deflected probe beam signal generated by laser-induced breakdown, comprising:
 a) generating laser-induced plasma by causing a pulse laser beam to be incident on a sample cell, which contains a standard nanoparticle having a known size, in a Z-axis direction so that the pulse laser beam is focused on an internal location of the sample cell, and causing a probe beam to be incident on the sample cell in a Y-axis direction perpendicular to a travel path of the pulse laser beam so that the probe beam passes through an internal location of the sample cell, spaced apart in an X-axis direction from a focus of the pulse laser beam by a predetermined distance;
 b) measuring signals of the probe beam, deflected by a laser-induced shock wave generated by the laser-induced plasma, using a photodiode;
 c) adjusting the focus of the pulse laser beam so that two signals, having collided against two walls of the sample cell located on an X-Y plane of the sample cell and then having reached the probe beam, among the deflected probe beam signals measured at b), overlap each other;
 d) obtaining symmetrical frequency distributions of magnitudes of a first deflected probe beam signal, appearing when the laser-induced shock wave directly reaches the probe beam, and a second deflected probe beam signal obtained at c), among the deflected probe beam signals measured at b), using a gate integrator;

e) performing curve fitting on the symmetrical frequency distribution of the magnitude of the first deflected probe beam signal obtained at d) to form a shape of a Gaussian function, and obtaining a peak and a full-width at half-maximum value from the curve-fitted distribution curve;

f) repeating a) to e) with respect to a standard nanoparticle having a size differing from that of the standard nanoparticle used at a) to e);

g) obtaining calibration curves by causing peaks and full-width at half-maximum values of curve-fitted distribution curves, respectively obtained at e) and f), to correspond to the sizes of the standard nanoparticles, respectively; and h) performing a) to e) with respect to an unknown particle, a size of which is unknown, and determining a size of the unknown nanoparticle using the calibration curves obtained at g).

6. The method according to claim 5, wherein a) to h) are performed on a nanoparticle having a size of less than 100 nm.

7. The method according to claim 5, wherein at a), a first linear polarizing plate installed to be rotatable and a second linear polarizing plate installed to fix a direction thereof so as to allow only a polarized laser beam traveling in an X-axis direction to pass therethrough are sequentially arranged on a path of the pulse laser beam before the pulse laser beam is incident on the sample cell, and energy of the pulse laser beam is adjusted by rotating the first linear polarizing plate.

8. The method according to claim 5, wherein at b), a light scattering signal corresponding to a wavelength of the pulse laser beam is blocked using a notch filter before signals of the probe beam having passed through the sample cell are detected by the photodiode.

9. The method according to claim 5, wherein at b), a lower portion of the probe beam deviating from a center portion thereof is detected by the photodiode.

10. A method of measuring a size of nanoparticles using a frequency distribution curve of a magnitude of a deflected probe beam signal generated by laser-induced breakdown, comprising:

a) generating laser-induced plasma by causing a pulse laser beam to be incident on a sample cell, which contains a standard nanoparticle having a known size, in a Z-axis direction so that the pulse laser beam is focused on an internal location of the sample cell, and causing a probe beam to be incident on the sample cell in a Y-axis direction perpendicular to a travel path of the pulse laser beam so that the probe beam passes through an internal location of the sample cell, spaced apart in an X-axis direction from a focus of the pulse laser beam by a predetermined distance;

b) measuring signals of the probe beam, deflected by a laser-induced shock wave generated by the laser-induced plasma, using a photodiode;

c) adjusting the focus of the pulse laser beam so that two signals, having collided against two walls of the sample cell located on an X-Y plane of the sample cell and then having reached the probe beam, among the deflected probe beam signals measured at b), overlap each other;

d) obtaining symmetrical frequency distributions of magnitudes of a first deflected probe beam signal, appearing when the laser-induced shock wave directly reaches the probe beam, and a second deflected probe beam signal obtained at c), among the deflected probe beam signals measured at b), using a gate integrator;

e) performing curve fitting on the symmetrical frequency distribution of the magnitude of the second deflected probe beam signal obtained at d) to form a shape of a Gaussian function, and obtaining a peak and a full-width half-maximum value from the curve-fitted distribution curve;

f) repeating a) to e) with respect to a standard nanoparticle having a size differing from that of the standard nanoparticle used at a) to e);

g) obtaining calibration curves by causing peaks and full-width at half-maximum values of curve-fitted distribution curves, respectively obtained at e) and f), to correspond to the sizes of the standard nanoparticles, respectively; and h) performing a) to e) with respect to an unknown particle, a size of which is unknown, and determining a size of the unknown nanoparticle using the calibration curves obtained at g).

11. The method according to claim 10, wherein a) to h) are performed on a nanoparticle having a size of less than 100 nm.

12. The method according to claim 10, wherein at a), a first linear polarizing plate installed to be rotatable and a second linear polarizing plate installed to fix a direction thereof so as to allow only a polarized laser beam traveling in an X-axis direction to pass therethrough are sequentially arranged on a path of the pulse laser beam before the pulse laser beam is incident on the sample cell, and energy of the pulse laser beam is adjusted by rotating the first linear polarizing plate.

13. The method according to claim 10, wherein at b), a light scattering signal corresponding to a wavelength of the pulse laser beam is blocked using a notch filter before signals of the probe beam having passed through the sample cell are detected by the photodiode.

14. The method according to claim 10, wherein at b), a lower portion of the probe beam deviating from a center portion thereof is detected by the photodiode.

* * * * *

UNITED STATES PATENT AND TRADEMARK OFFICE
CERTIFICATE OF CORRECTION

PATENT NO. : 7,679,743 B1 Page 1 of 1
APPLICATION NO. : 12/345424
DATED : March 16, 2010
INVENTOR(S) : Euo Chang Jung et al.

It is certified that error appears in the above-identified patent and that said Letters Patent is hereby corrected as shown below:

Title Page at section 30 (Foreign Application Priority Data section), line 1, please change "Jan. 31, 2008 (KR).............10-2008-0009957" to -- Oct. 10, 2008 (KR).............10-2008-0099572 --.

Signed and Sealed this

Fourth Day of May, 2010

David J. Kappos
*Director of the United States Patent and Trademark Office*